US011623076B2

United States Patent
Gill et al.

(10) Patent No.: US 11,623,076 B2
(45) Date of Patent: Apr. 11, 2023

(54) TAILORABLE MEDICINALLY COATED FLOSS FOR THE TREATMENT OF GUM DISEASE

(71) Applicant: Texas Tech University System, Lubbock, TX (US)

(72) Inventors: Harvinder Singh Gill, Lubbock, TX (US); Seth Boese, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 17/050,961

(22) PCT Filed: May 1, 2019

(86) PCT No.: PCT/US2019/030250
§ 371 (c)(1),
(2) Date: Oct. 27, 2020

(87) PCT Pub. No.: WO2019/213298
PCT Pub. Date: Nov. 7, 2019

(65) Prior Publication Data
US 2021/0228848 A1 Jul. 29, 2021

Related U.S. Application Data

(60) Provisional application No. 62/665,060, filed on May 1, 2018.

(51) Int. Cl.
*A61M 31/00* (2006.01)
*A61K 9/00* (2006.01)
*A61K 9/48* (2006.01)
*A61K 9/70* (2006.01)
*A61K 47/34* (2017.01)
*A61K 31/352* (2006.01)

(52) U.S. Cl.
CPC ........... *A61M 31/00* (2013.01); *A61K 9/0053* (2013.01); *A61K 9/4891* (2013.01); *A61K 9/70* (2013.01); *A61K 47/34* (2013.01); *A61K 31/352* (2013.01)

(58) Field of Classification Search
CPC ... A61M 31/00; A61K 9/0053; A61K 9/4891; A61K 9/70; A61K 47/34; A61K 31/352
See application file for complete search history.

(56) References Cited

U.S. PATENT DOCUMENTS

| 5,603,921 A | 2/1997 | Bowen |
| 5,692,530 A | 12/1997 | Bible et al. |
| 5,875,799 A | 3/1999 | Petrus |
| 6,575,176 B1 * | 6/2003 | Hill ......................... A61Q 11/00 |
| | | 132/321 |
| 2004/0163664 A1 | 8/2004 | Husted |
| 2005/0087208 A1 | 4/2005 | Satary-Ravabakhsh |
| 2013/0058983 A1 * | 3/2013 | Baker .................. A61K 9/0014 |
| | | 514/192 |

FOREIGN PATENT DOCUMENTS

WO 99/32046 A1 7/1999

OTHER PUBLICATIONS

Chapple, ILC et al (2015) Primary prevention of periodontitis: managing gingivitis. Journal Clinical Peridontology 42 (Suppl. 16), 71-76.
Eke Pi et al. Prevalence of periodontitis in adults in the United States: 2009 and 2010. J Dent Res. 2012;91 (10):914-920.
Kinane, D et al. (2005) Advances in the pathogenesis of periodontitis. Group B consensus report of the fifth European Workshop in Periodontology. Journal of Clinical Periodontology 32(Suppl. 6), 130-131.
International Search Report, PCT/2019/30250 [ISA/US] dated Aug. 28, 2019.
Mori et al. Preparation of Serial Carbowax Sections for Fat-Staining: A Combined Gelatin Carbowax-Paraffin Technic.? The tohoku Journal of Experimental Medicine, vol. 71(4). 1960. pp. 359-362.

* cited by examiner

*Primary Examiner* — Robert A Wax
*Assistant Examiner* — Olga V. Tcherkasskaya
(74) *Attorney, Agent, or Firm* — Edwin S. Flores; Daniel J. Chalker; Chalker Flores, LLP

(57) ABSTRACT

The present invention includes a medicated dental floss and a method of making a medicated dental floss comprising: stretching a dental floss; dipping the dental floss in a biocompatible polymer—solvent bath to coat the braided dental floss; drying the coated braided dental floss; dipping the coated dental floss in a medicated solution comprising an encapsulated medicament; and drying the medicated encapsulant on the coated dental floss.

10 Claims, 7 Drawing Sheets

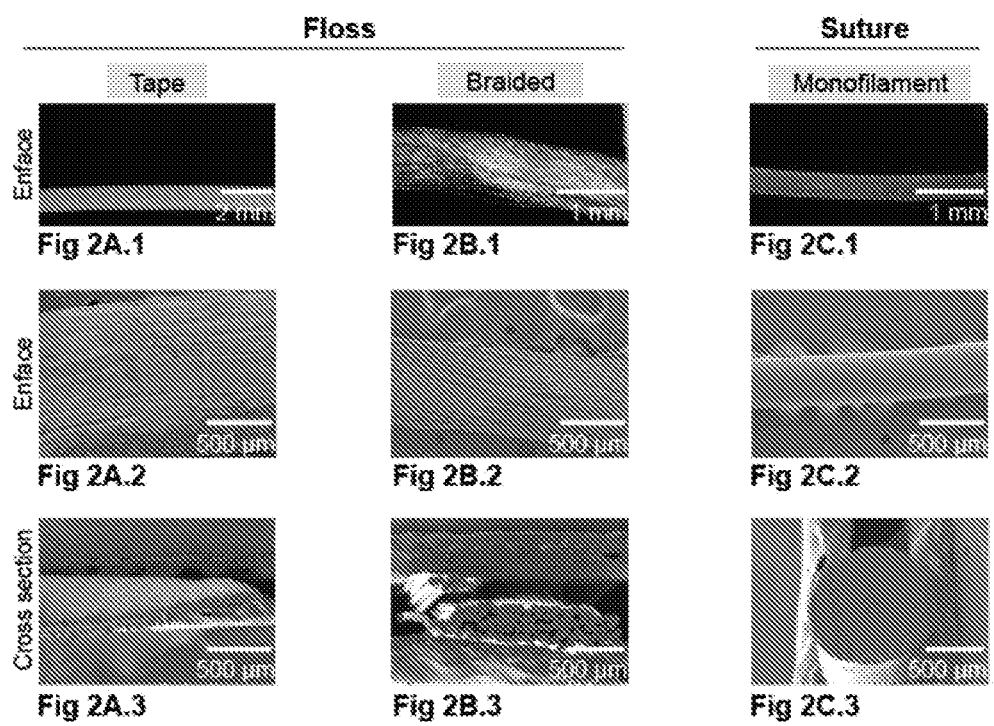
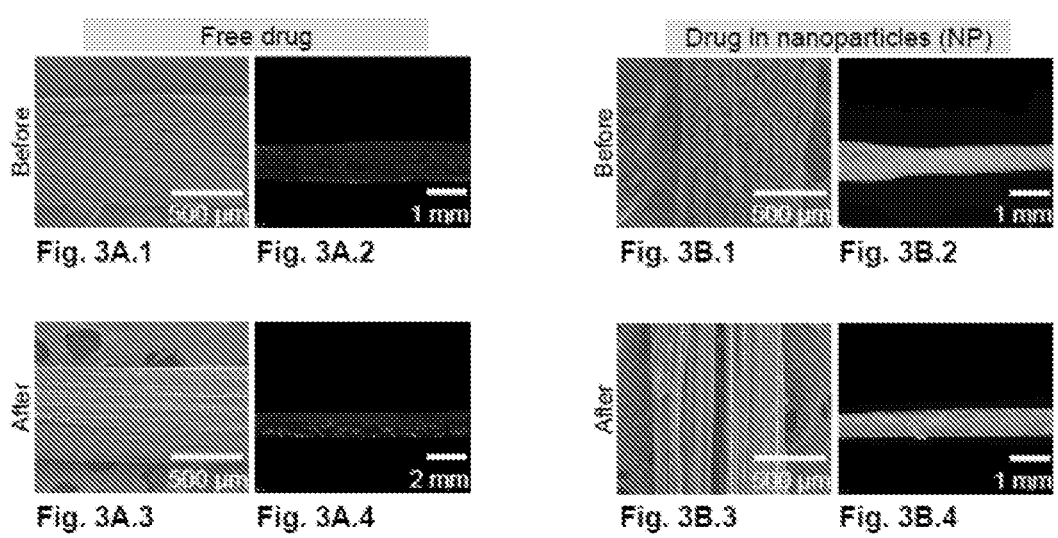

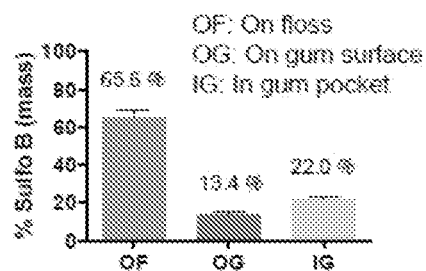
Fig. 4A
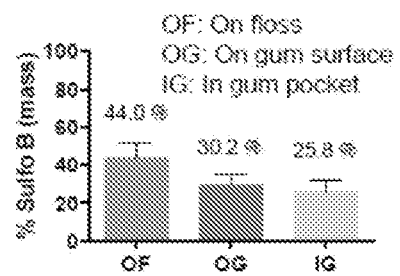
Fig. 4B
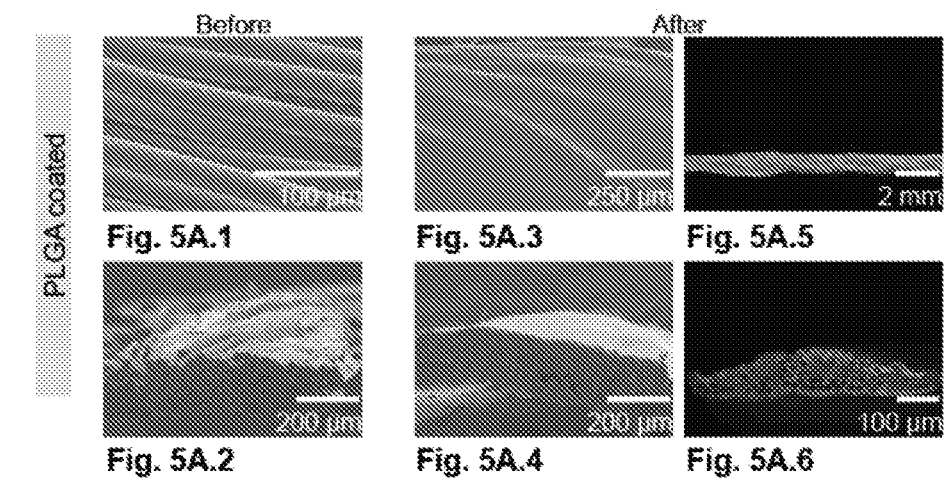
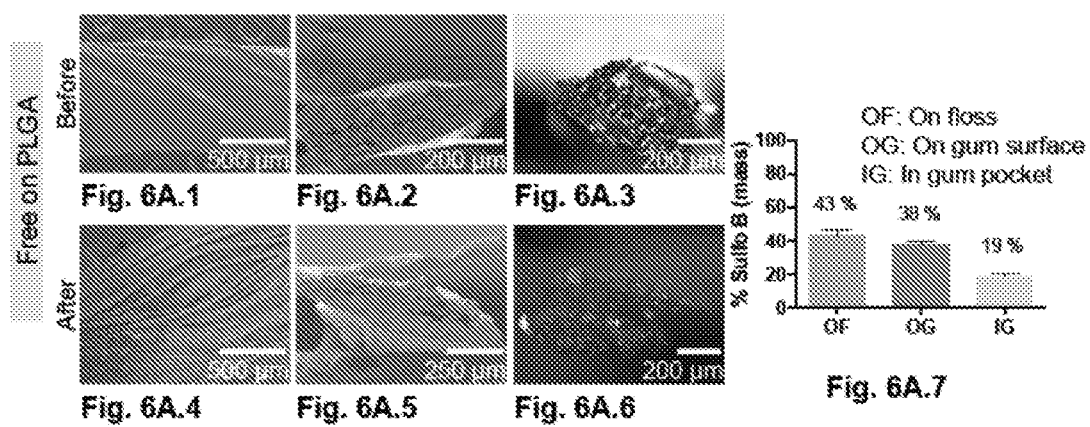

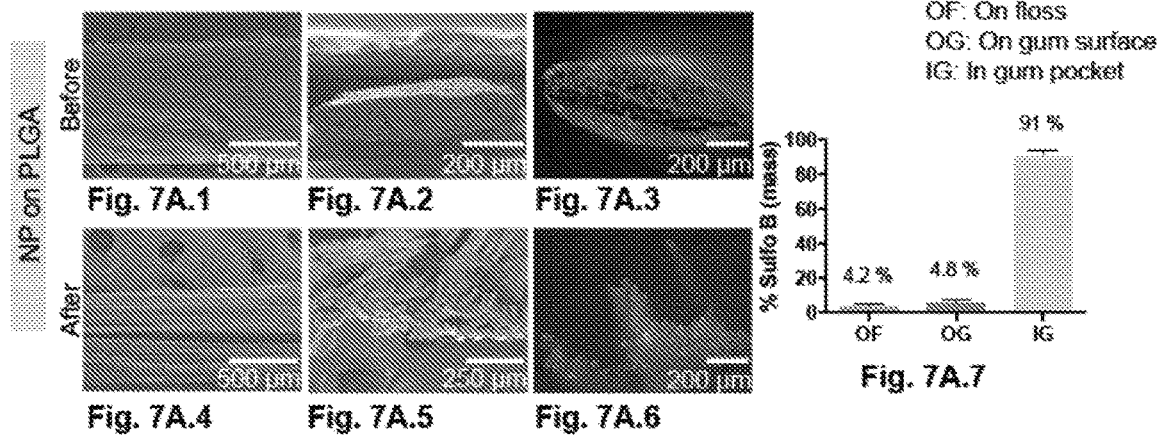
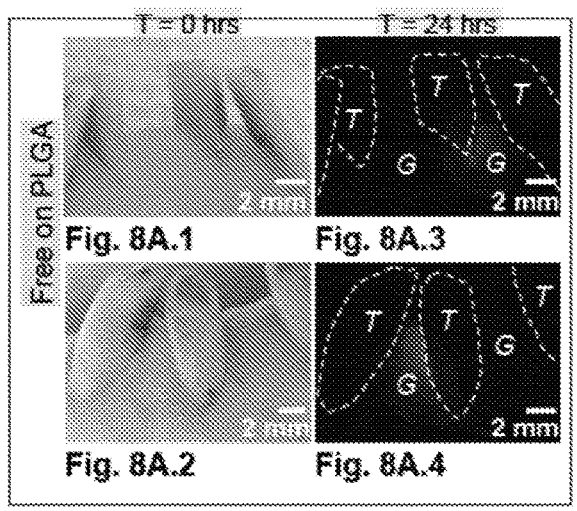
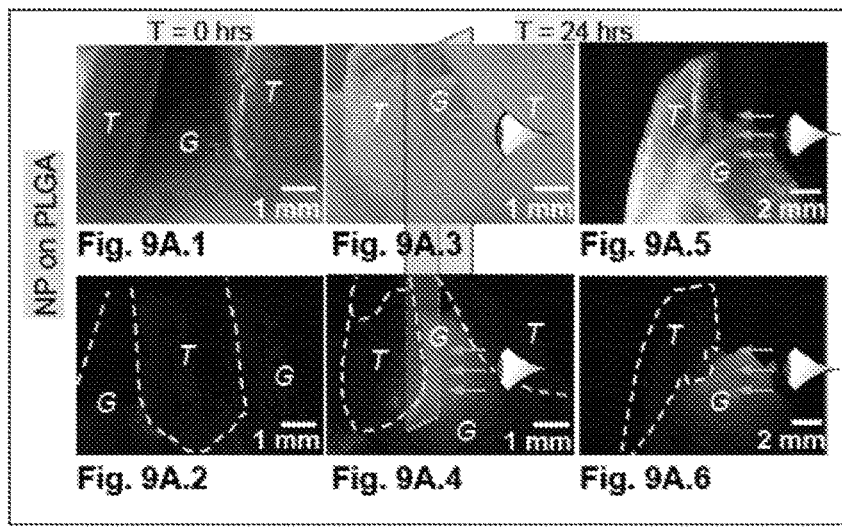

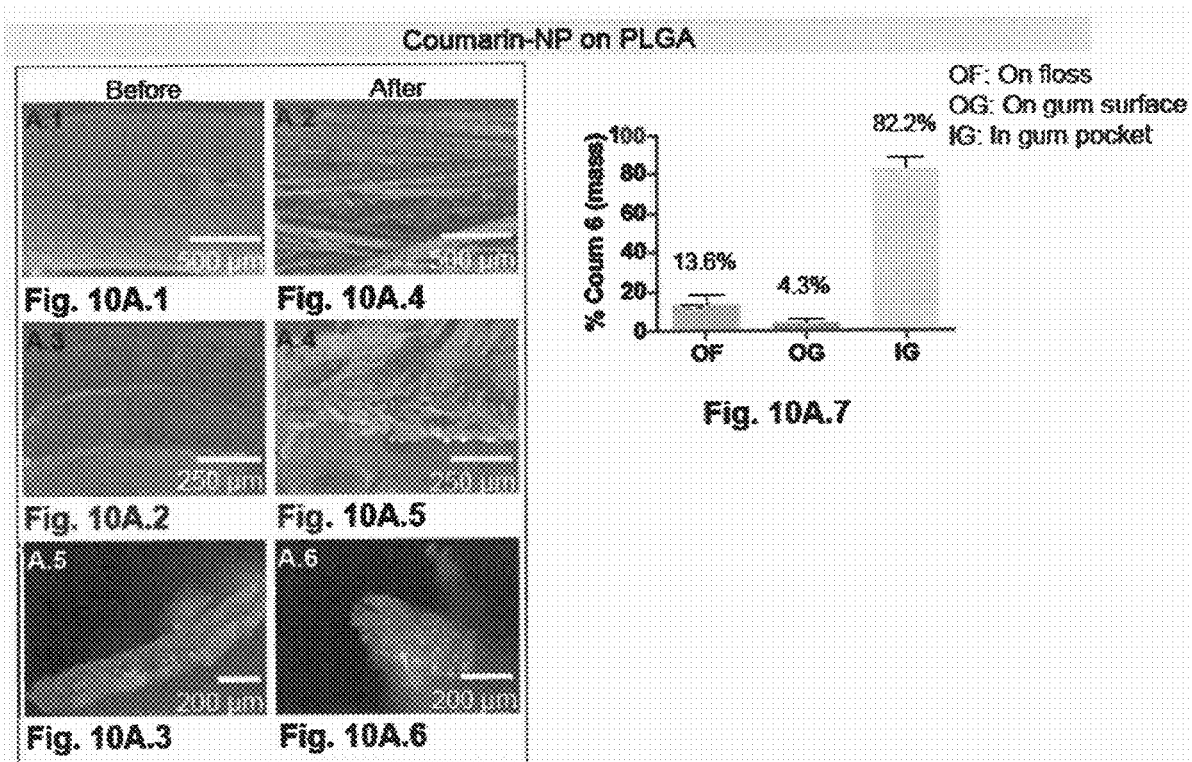
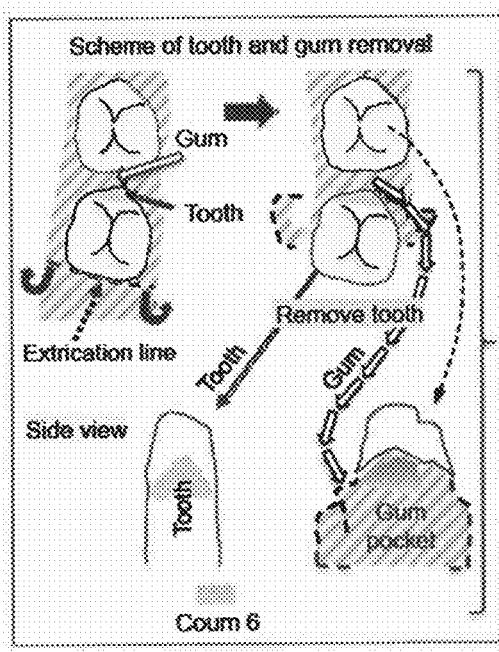
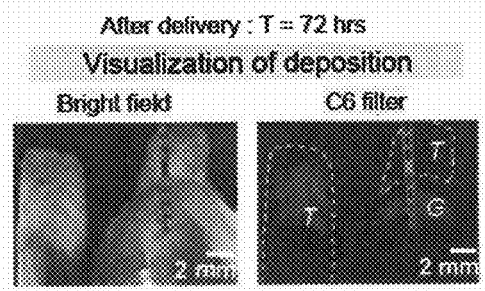
Fig. 11A.1
Fig. 11A.2  Fig. 11A.3

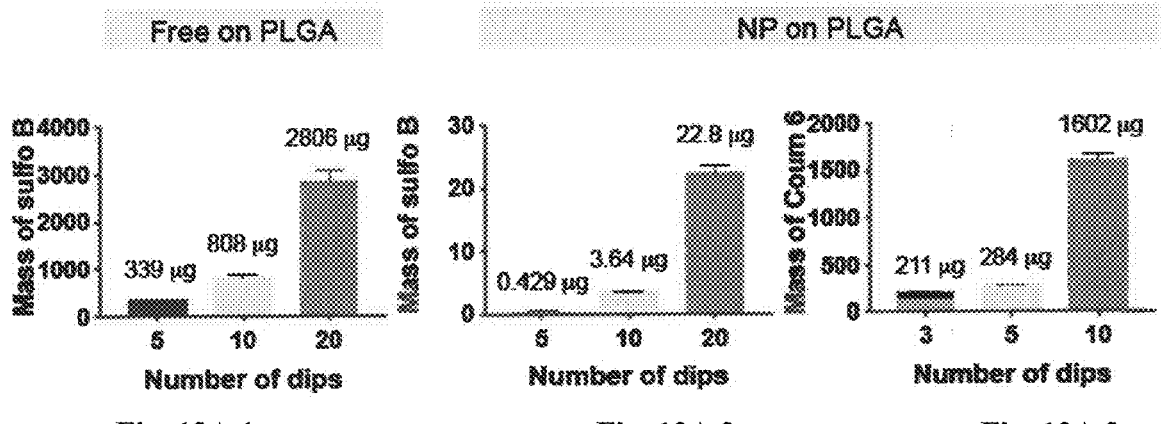
Fig. 12A.1  Fig. 12A.2  Fig. 12A.3
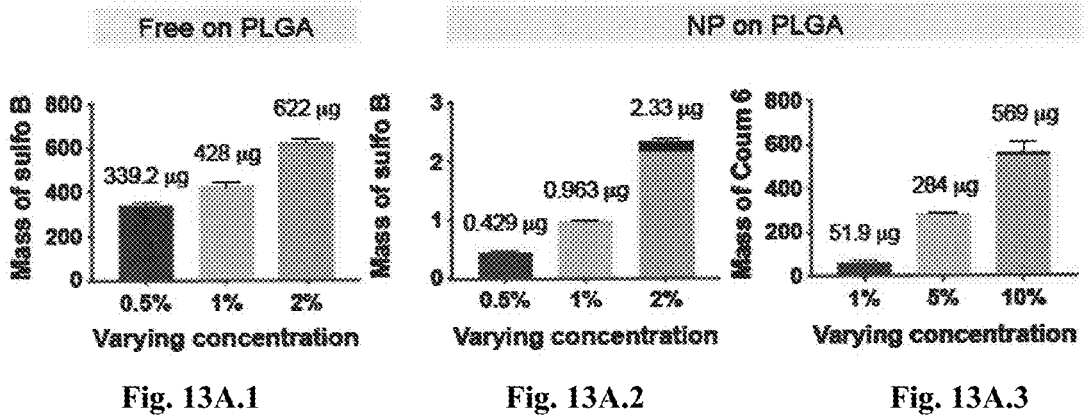
Fig. 13A.1  Fig. 13A.2  Fig. 13A.3
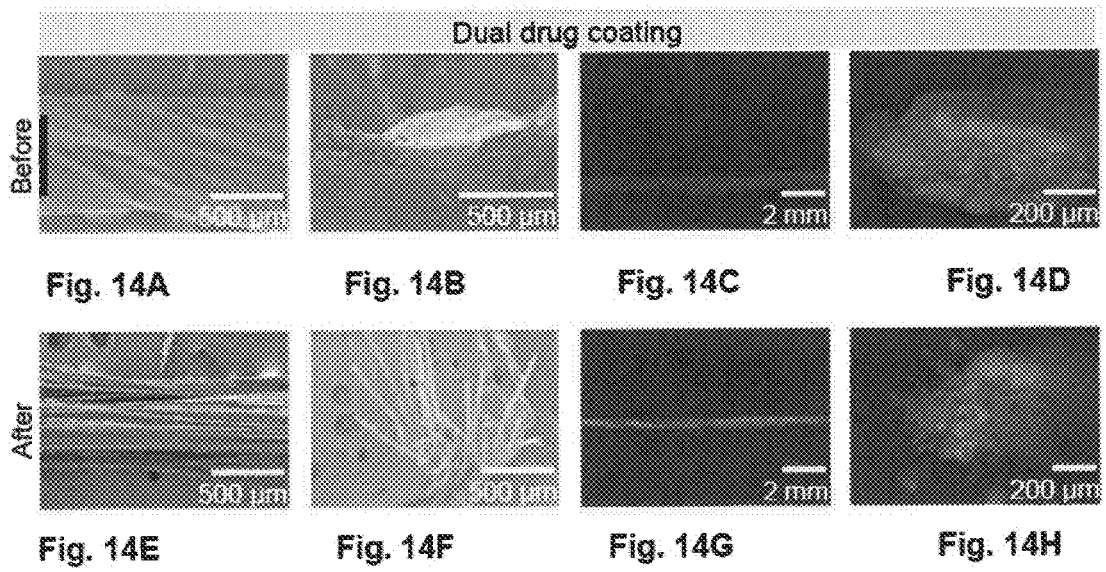
Fig. 14A  Fig. 14B  Fig. 14C  Fig. 14D
Fig. 14E  Fig. 14F  Fig. 14G  Fig. 14H

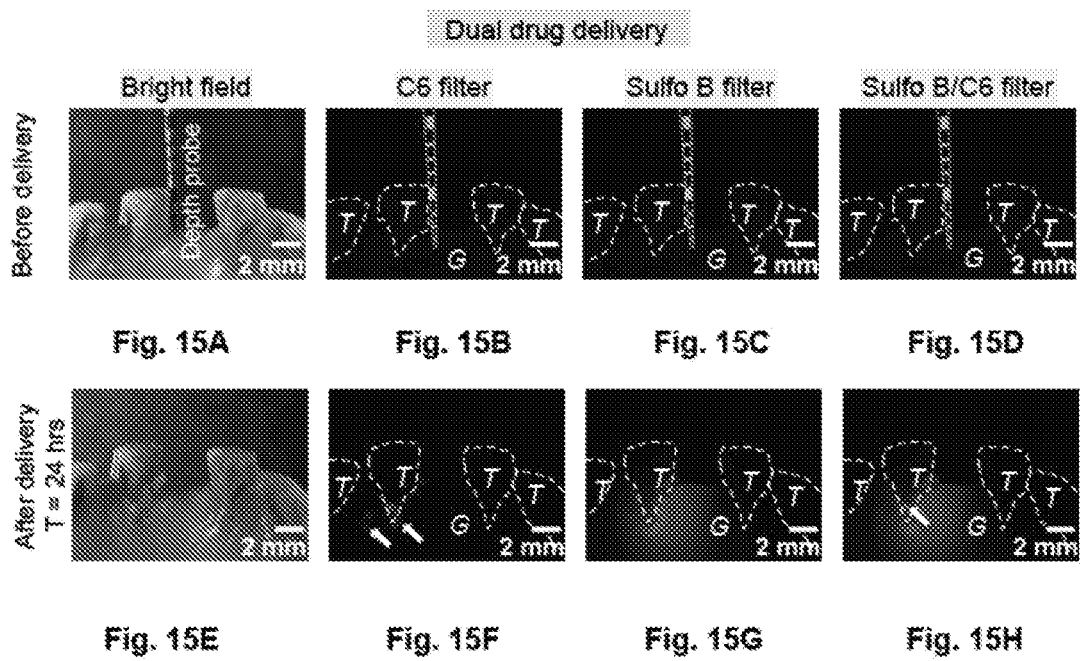
Fig. 15A   Fig. 15B   Fig. 15C   Fig. 15D
Fig. 15E   Fig. 15F   Fig. 15G   Fig. 15H
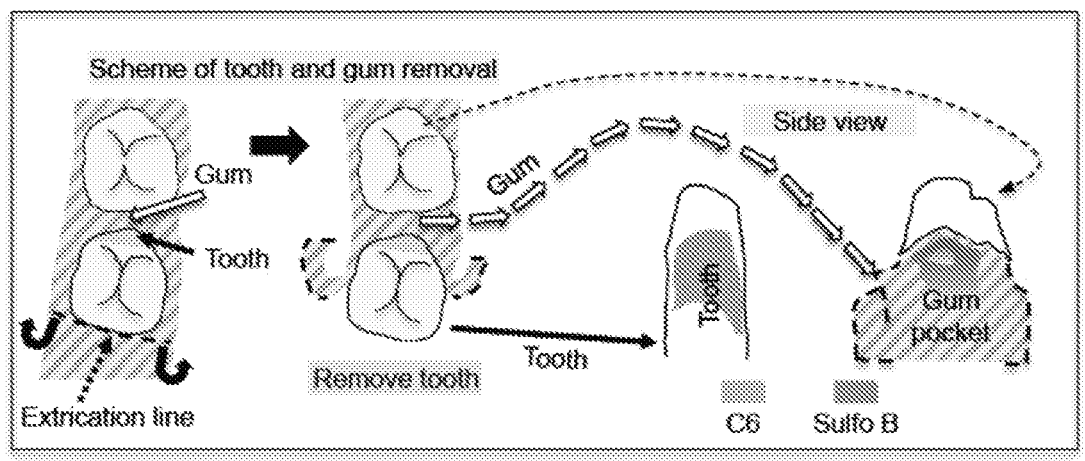
Fig. 16A
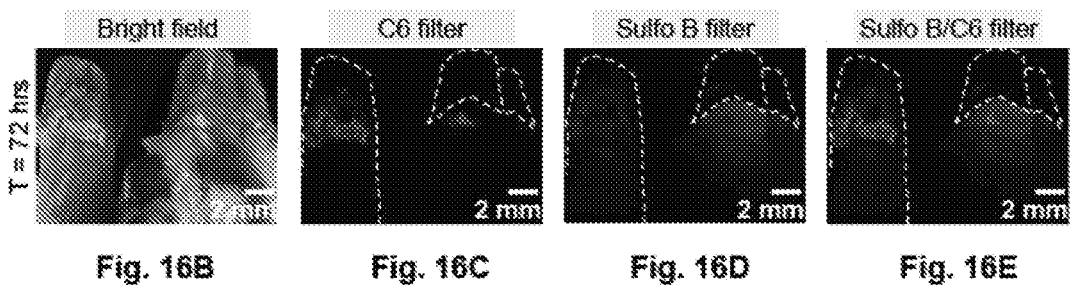
Fig. 16B   Fig. 16C   Fig. 16D   Fig. 16E

TAILORABLE MEDICINALLY COATED FLOSS FOR THE TREATMENT OF GUM DISEASE

CROSS-REFERENCE TO RELATED APPLICATIONS

This application claims priority to and is the National Stage of International Application No. PCT/US2019/030250, filed on May 1, 2019 and claims priority to U.S. Provisional Application Ser. No. 62/665,060, filed May 1, 2018, the entire contents of which are incorporated herein by reference.

TECHNICAL FIELD OF THE INVENTION

The present invention relates in general to the field of treatments for gum disease, and more particularly, to medically modified or coated floss for the treatment of gum diseases.

BACKGROUND OF THE INVENTION

Without limiting the scope of the invention, its background is described in connection with gum disease.

Gum disease is a common problem that affects 70% of people over 65. As we age, the risk becomes greater. This can lead to all kinds of problems including tooth loss, diabetes, and heart disease. As with most health issues, prevention is the best method of treatment. However, once the disease is contracted, there are a few options to treat it.

Currently, options for treatment of gum disease include: (1) professional cleaning by dentist; (2) scaling and root planning (requiring local anesthesia); (3) systemic medication delivery (e.g. taking an antibiotic pill); (4) local delivery of medication (injection of a medicated gel within the gum line that requires a dentist visit); (5) blue light therapy (otherwise known as laser light or Er:YAG light therapy); or (6) surgical removal of necrotic tissue followed by tissue grafting. However, none of these techniques truly addresses the problem due to the persistence and constant reintroduction of harmful bacteria. Most of these are fairly invasive so it is clear that a better solution is needed.

SUMMARY OF THE INVENTION

In one embodiment, the present invention includes a method of treating gum disease, comprising, consisting essentially of, or consisting of: providing a flexible filament, wherein at least part of the filament is uniformly coated with a drug; inserting the filament into a gum pocket; and moving the filament in the gum pocket at least once to deposit at least part of the drug from the filament into the gum pocket. In one aspect, the filament is selected from a thread, a floss, or a suture. In another aspect, the filament is a floss selected from unwaxed, waxed, braided, non-braided, monolithic, tape, or a combination thereof. In another aspect, the coated portion of the filament is moved more than once in and out of the gum pocket. In another aspect, the filament is of monolithic construction or comprises two or more filaments braided together. In another aspect, the drug is selected from an antibiotic, an antiinflammatory, an antimicrobial, an antifungal, an antibody, a steroid, an antiparasitic, an antiamoebic, an antihelminthic, an antiprotozoal, an antinematode, an anticestode, an antitrematode, or mixtures thereof. In another aspect, the antibiotic is selected from the group consisting of amikacin, betamethasone, clindamycin, clotrimazole, gentamicin, kanamycin, minocycline, oxytetracycline, penicillin, tetracycline and mixtures thereof. In another aspect, the drug in the coating is applied as free drug, the drug is entrapment in a particle, the drug is encapsulated, or a combination thereof. In another aspect, the filament before coating with drug is first coated with a precoat layer to alter surface energy of the filament surface to achieve uniform coating of the drug or to fill the voids in the filament surface so that drug is not trapped in the voids present in the filament or in between the filaments or to both alter the surface energy and fill the voids, and drug is coated on a precoat layer. In another aspect, a precoat layer also contains drug either in free form, after entrapment in particles, encapsulated, or a combination thereof. In another aspect, the method further includes securing the filament in the gum pocket for a pre-determined duration of time.

A method of making a medicated filament comprising, consisting essentially of, or consisting of: stretching the filament; dipping the filament in a biocompatible polymer—solvent bath to coat the filament; drying the coated filament; dipping the coated filament in a medicated solution comprising a medicament; and drying the medicament onto the coated filament. In one aspect, the filament is a floss selected from unwaxed, waxed, braided, non-braided, monolithic, tape, or a combination thereof. In another aspect, the filament is a coated dental floss dipped in the medicated solution at least three times. In another aspect, the biocompatible polymer is selected from polymers of hydroxy acids, lactic acid polymers, glycolic acid polymers, lactic acid and glycolic acid polymers, poly(hydroxyl acids), poly(lactic acid)_(PLA), poly(glycolic acid) (PGA), poly(lactic-co-glycolic acid)_(PLGA), and copolymers with polyethyleneglycol (PEG), polyanhydrides, poly(ortho)esters, polyesters, polyurethanes, poly(butyric acid), poly(valeric acid), poly (caprolactone), poly(hydroxyalkanoates, poly(lactide-co-caprolactone), blends and copolymers thereof, natural polymers, proteins, albumin, collagen, gelatin, prolamines, zein, polysaccharides, alginate, cellulose derivatives and polyhydroxyalkanoates, polyhydroxybutyrate blends, and copolymers thereof. In another aspect, the solvent is selected from dichloromethane, ethyl acetate, acetone, or a mixture thereof. In another aspect, the dental floss is selected from silk, cotton, ethylene vinyl acetate, polyvinyl alcohols, teflon, nylon, polymethacrylate, polystyrene, polypropylene, polyterepthalate, and silicon polymers. In another aspect, the an encapsulant for the medicament is selected from one or more polymers selected from the group consisting of poly (hydroxy acids), PLA, PGA, PLGA, poly(lactic-co-glycolic acid), derivatives of poly(lactic-co-glycolic acid), PEGylated poly(lactic-co-glycolic acid), poly(lactide), poly(glycolide), poly(lactide-co-glycolide), poly(anhydrides), PEGylated poly(anhydrides), poly (ortho esters), derivatives of poly(ortho esters), PEGylated poly(ortho esters), poly (caprolactones), derivatives of poly(caprolactone), PEGylated poly(caprolactones), polyamines, spermine, spermidine, polylysine, and derivatives thereof, PEGylated polylysine, polyamides, polycarbonates, poly(propylene fumarates), polyamides, polyphosphazenes, polyamino acids, polyethers, polyacetals, polylactides, polyhydroxyalkanoates, polyglycolides, polyketals, polyesteramides, poly (dioxanones), polyhydroxybutyrates, polyhydroxyvalyrates, polycarbonates, polyorthocarbonates, poly(vinyl pyrrolidone), polycyanoacrylates, polyalkylene oxalates, polyalkylene succinates, poly(malic acid), poly(methyl vinyl ether), poly(ethylene imine), poly(acrylic acid), poly(maleic anhydride), poly(ethylene imine), derivatives of poly(ethylene imine), PEGylated poly(ethylene imine), poly(acrylic acid), derivatives of poly(acrylic acid), PEGylated poly(acrylic acid), poly(urethane), PEGylated poly(urethane), derivatives of poly(urethane), poly(lactide), poly(glycolide), poly(hydroxy acids), polyesters, poly(arylates), polyalkylenes, polyethylene, polypropylene, polyalkylene glycols, poly(ethylene glycol), polyalkylene oxides such as poly(ethylene oxide), polyalkylene terepthalates, poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses, alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, polymers of acrylic acid, methacrylic acid or copolymers or derivatives thereof, methacrylic acid esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(butyric acid), poly(valeric acid), and poly(lactide-co-caprolactone) and/or derivatives thereof, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and/or combinations thereof, natural polymers, proteins (such as albumin, collagen, gelatin), prolamines (for example, zein), polysaccharides (such as alginate), cellulose derivatives (such as hydroxypropyl cellulose, sodium carboxymethyl cellulose, ethyl cellulose and cellulose acetate), polyhydroxyalkanoates (for example, polyhydroxybutyrate), and/or combinations thereof. In another aspect, the drug is selected from an antibiotic, an antiinflammatory, an antimicrobial, an antifungal, an antibody, a steroid, an antiparasitic, an antiamoebic, an antihelminthic, an antiprotozoal, an antinematode, an anticestode, an antitrematode or mixtures thereof. In another aspect, the antibiotic is selected from the group consisting of amikacin, betamethasone, clindamycin, clotrimazole, gentamicin, kanamycin, minocycline, oxytetracycline, penicillin, tetracycline and mixtures thereof.

Yet another embodiment of the present invention includes a method of making a medicated dental floss comprising, consisting essentially of, or consisting of: stretching a dental floss; dipping the dental floss in a biocompatible polymer—solvent bath to coat the braided dental floss; drying the coated dental floss; dipping the coated dental floss in a medicated solution comprising an encapsulated medicament; and drying the medicated encapsulant on the coated dental floss.

BRIEF DESCRIPTION OF THE DRAWINGS

For a more complete understanding of the features and advantages of the present invention, reference is now made to the detailed description of the invention along with the accompanying figures and in which:

FIGS. 2A, 2B, and 2C show images of different examples of floss and sutures. 2A.1, 2A.2, and 2A.3 show enface (surface) brightfield micrograph, enface (surface) scanning electron micrograph, and scanning electron micrograph of cross section of a tape-architecture floss. 2B.1, 2B.2, and 2B.3 show enface (surface) brightfield micrograph, enface (surface) scanning electron micrograph, and scanning electron micrograph of cross section of a braided-architecture floss. 2C.1, 2C.2, and 2C.3 show enface (surface) brightfield micrograph, enface (surface) scanning electron micrograph, and scanning electron micrograph of cross section of a monofilament suture.

FIGS. 3A and 3B including 3A.1 3A.2, 3A.3, 3A.4, 3B.1, 3B.2, 3B.3, 3B.4 show images of floss coated with free drug and floss coated with nanoparticles encapsulating drug. (FIG. 3A) (FIG. 3A) Images of floss coated with free sulforhodamine drug. (FIG. 3A.1) scanning electron micrograph of floss coated with free sulforhodamine before flossing. (FIG. 3A.2) Fluorescent micrograph of floss coated with free sulforhodamine before flossing. (FIG. 3A.3) Scanning electron micrograph of floss coated with free sulforhodamine after flossing porcine teeth. (FIG. 3A.4) Fluorescent micrograph of floss coated with free sulforhodamine after flossing porcine teeth. (FIG. 3B) Images of floss coated with poly(lactic-co-glycolic) acid nanoparticles encapsulating sulforhodamine drug. (FIG. 3B.1) scanning electron micrograph of floss coated with poly(lactic-co-glycolic) acid nanoparticles encapsulating sulforhodamine drug before flossing. (FIG. 3B.2) Fluorescent micrograph of floss coated with poly(lactic-co-glycolic) acid nanoparticles encapsulating sulforhodamine drug before flossing. (FIG. 3B.3) Scanning electron micrograph of floss coated with poly(lactic-co-glycolic) acid nanoparticles encapsulating sulforhodamine drug after flossing porcine teeth. (FIG. 3B.4) Fluorescent micrograph of floss coated with poly(lactic-co-glycolic) acid nanoparticles encapsulating sulforhodamine drug after flossing porcine teeth.

FIGS. 4A, 4B, show delivery efficiency of floss coated with free sulforhodamine or poly(lactic-co-glycolic) acid nanoparticles encapsulating sulforhodamine drug. (FIG. 4A) Delivery efficiency of floss coated with free sulforhodamine after flossing porcine teeth. (FIG. 4B) Delivery efficiency of floss coated with poly(lactic-co-glycolic) acid nanoparticles encapsulating sulforhodamine drug after flossing porcine teeth.

FIGS. 5A.1 to 5A.6 show images of braided floss before and after a precoat layer of poly(lactic-co-glycolic) acid to fill the voids between individual braids in the floss. (FIG. 5A.1) Scanning electron micrograph of braided floss before coating with poly(lactic-co-glycolic) acid. (FIG. 5A.1) Scanning electron micrograph of braided floss surface before coating with poly(lactic-co-glycolic) acid. (FIG. 5A.2) Scanning electron micrograph of braided floss cross section before coating with poly(lactic-co-glycolic) acid. (FIG. 5A.3) Scanning electron micrograph of braided floss surface after coating with poly(lactic-co-glycolic) acid. (FIG. 5A.4) Scanning electron micrograph of braided floss cross section after coating with poly(lactic-co-glycolic) acid. (FIG. 5A.5) Fluorescent micrograph of braided floss surface after coating with poly(lactic-co-glycolic) acid. (FIG. 5A.6)

Figure 1A:
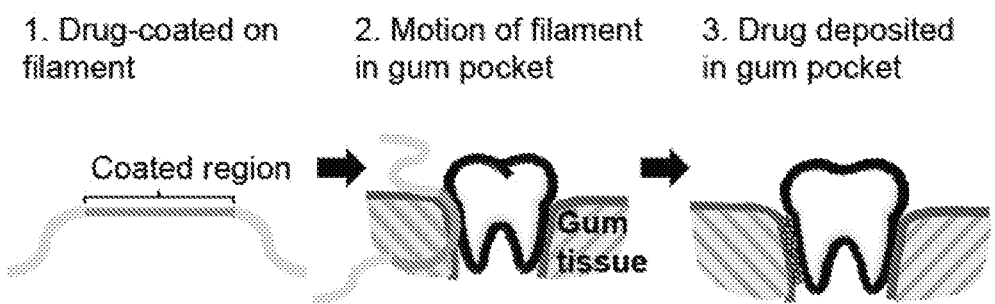
FIGS. 1A and 1B show two example embodiments of use of flexible filament for drug delivery in to the gum pocket. In one embodiment (FIG. 1A) the filament is moved in the gum pocket, and in another embodiment the flexible filament is secured in the gum pocket (FIG. 1B).

Fluorescent micrograph of braided floss cross section after coating with poly(lactic-co-glycolic) acid.

FIGS. 6A.1 to 6A.7 show images and delivery efficiency of braided floss coated with a precoat of poly(lactic-co-glycolic), then coated with free sulforhodamine on top, and then subjected to flossing of porcine teeth. (FIG. 6A.1) Scanning electron micrograph of surface of braided floss coated with a precoat of poly(lactic-co-glycolic) and subsequently coated with free sulforhodamine before flossing of procine teeth. (FIG. 6A.2) Scanning electron micrograph of cross section of braided floss coated with a precoat of poly(lactic-co-glycolic) and subsequently coated with free sulforhodamine before flossing of procine teeth. (FIG. 6A.3) Fluorescent micrograph of cross section of braided floss coated with a precoat of poly(lactic-co-glycolic) and subsequently coated with free sulforhodamine before flossing of procine teeth. (FIG. 6A.4) Scanning electron micrograph of surface of braided floss coated with a precoat of poly(lactic-co-glycolic) and subsequently coated with free sulforhodamine after flossing of procine teeth. (FIG. 6A.5) Scanning electron micrograph of cross section of braided floss coated with a precoat of poly(lactic-co-glycolic) and subsequently coated with free sulforhodamine after flossing of procine teeth. (FIG. 6A.6) Fluorescent micrograph of cross section of braided floss coated with a precoat of poly(lactic-co-glycolic) and subsequently coated with free sulforhodamine after flossing of procine teeth. (FIG. 6A.7) Delivery efficiency of braided floss coated with a precoat of poly(lactic-co-glycolic) and subsequently coated with free sulforhodamine after flossing of procine teeth.

FIGS. 7A.1 to 7A.7 show images and delivery efficiency of braided floss coated with a precoat of poly(lactic-co-glycolic), then coated with poly(lactic-co-glycolic) acid nanoparticles encapsulating sulforhodamine drug on top, and then subjected to flossing of porcine teeth. (FIG. 7A.1) Scanning electron micrograph of surface of braided floss coated with a precoat of poly(lactic-co-glycolic) and subsequently coated with poly(lactic-co-glycolic) acid nanoparticles encapsulating sulforhodamine drug, before flossing of procine teeth. (FIG. 7A.2) Scanning electron micrograph of cross section of braided floss coated with a precoat of poly(lactic-co-glycolic) and subsequently coated with poly(lactic-co-glycolic) acid nanoparticles encapsulating sulforhodamine drug, before flossing of procine teeth. (FIG. 7A.3) Fluorescent micrograph of cross section of braided floss coated with a precoat of poly(lactic-co-glycolic) and subsequently coated with poly(lactic-co-glycolic) acid nanoparticles encapsulating sulforhodamine drug before flossing of procine teeth. (FIG. 7A.4) Scanning electron micrograph of surface of braided floss coated with a precoat of poly(lactic-co-glycolic) and subsequently coated with poly(lactic-co-glycolic) acid nanoparticles encapsulating sulforhodamine drug after flossing of procine teeth. (FIG. 7A.5) Scanning electron micrograph of cross section of braided floss coated with a precoat of poly(lactic-co-glycolic) and subsequently coated with poly(lactic-co-glycolic) acid nanoparticles encapsulating sulforhodamine drug after flossing of porcine teeth. (FIG. 7A.6) Fluorescent micrograph of cross section of braided floss coated with a precoat of poly(lactic-co-glycolic) and subsequently coated with poly(lactic-co-glycolic) acid nanoparticles encapsulating sulforhodamine drug after flossing of procine teeth. (FIG. 7A.7) Delivery efficiency of braided floss coated with a precoat of poly(lactic-co-glycolic) and subsequently coated with poly(lactic-co-glycolic) acid nanoparticles encapsulating sulforhodamine drug after flossing of procine teeth. FIG. 8A.1 to 8A.4 shows visual proof of delivery of free sulforhodamine into porcine gum pocket after flossing with a braided floss that was coated with a precoat of poly(lactic-co-glycolic), then coated with free sulforhodamine on top. (FIG. 8A.1) Photograph of porcine teeth before flossing, looking from inside the mouth. (FIG. 8A.2) Photograph of porcine teeth before flossing, looking from outside the mouth. (FIG. 8A.3) Fluorescent micrograph of porcine teeth 24 h after flossing, looking from inside the mouth. (FIG. 8A.4) Fluorescent micrograph of porcine teeth 24 h after flossing, looking from outside the mouth. I FIG. 9A.1 to 9A.6 shows visual proof of delivery of poly(lactic-co-glycolic) acid nanoparticles encapsulating sulforhodamine drug into porcine gum pocket after flossing with a braided floss that was coated with a precoat of poly(lactic-co-glycolic), then coated with poly(lactic-co-glycolic) acid nanoparticles encapsulating sulforhodamine drug on top. (FIG. 9A.1) Photograph of porcine teeth before flossing. (FIG. 9A.2) Fluorescent micrograph of porcine teeth before flossing. (FIG. 9A.3) Photograph of porcine teeth 24 h after flossing. (FIG. 9A.4) Fluorescent micrograph of porcine teeth 24 h after flossing. (FIG. 9A.5) Photograph of porcine teeth 24 h after flossing and after the surrounding gum tissue was cut away. (FIG. 9A.6) Fluorescent micrograph of porcine teeth 24 h after flossing and after the surrounding gum tissue was cut away.

FIG. 10A.1 to 10A.7 show images and delivery efficiency of braided floss coated with a precoat of poly(lactic-co-glycolic), then coated with poly(lactic-co-glycolic) acid nanoparticles encapsulating coumarin 6 drug on top, and then subjected to flossing of porcine teeth. (FIG. 10A.1) Scanning electron micrograph of surface of braided floss coated with a precoat of poly(lactic-co-glycolic) and subsequently coated with poly(lactic-co-glycolic) acid nanoparticles encapsulating coumarin 6 drug, before flossing of procine teeth. (FIG. 10A.2) Scanning electron micrograph of cross section of braided floss coated with a precoat of poly(lactic-co-glycolic) and subsequently coated with poly(lactic-co-glycolic) acid nanoparticles encapsulating coumarin 6 drug, before flossing of procine teeth. (FIG. 10A.3) Fluorescent micrograph of cross section of braided floss coated with a precoat of poly(lactic-co-glycolic) and subsequently coated with poly(lactic-co-glycolic) acid nanoparticles encapsulating coumarin 6 drug before flossing of procine teeth. (FIG. 10A.4) Scanning electron micrograph of surface of braided floss coated with a precoat of poly(lactic-co-glycolic) and subsequently coated with poly(lactic-co-glycolic) acid nanoparticles encapsulating coumarin 6 drug after flossing of procine teeth. (FIG. 10A.5) Scanning electron micrograph of cross section of braided floss coated with a precoat of poly(lactic-co-glycolic) and subsequently coated with poly(lactic-co-glycolic) acid nanoparticles encapsulating coumarin 6 drug after flossing of procine teeth. (FIG. 10A.6) Fluorescent micrograph of cross section of braided floss coated with a precoat of poly(lactic-co-glycolic) and subsequently coated with poly(lactic-co-glycolic) acid nanoparticles encapsulating coumarin 6 drug after flossing of procine teeth. (FIG. 10A.7) Delivery efficiency of braided floss coated with a precoat of poly(lactic-co-glycolic) and subsequently coated with poly(lactic-co-glycolic) acid nanoparticles encapsulating coumarin 6 drug after flossing of procine teeth.

FIG. 11A.1 to 11A.3 shows visual proof of delivery of poly(lactic-co-glycolic) acid nanoparticles encapsulating coumarin 6 drug into porcine gum pocket after flossing with a braided floss coated with a precoat of poly(lactic-co-glycolic) and subsequently coated with poly(lactic-co-glycolic) acid nanoparticles encapsulating coumarin 6 drug after flossing of procine teeth. (FIG. 11A.1) Scheme for cutting the gum and extracting teeth for visualization. (FIG. 11A.2) Brightfield micrograph of extracted tooth and gum pocket 72 hours after flossing. (FIG. 11A.3) Fluorescent micrograph of extracted tooth and gum pocket 72 hours after flossing.

FIG. 12A.1 to 12A.3 show effect of number of times the floss is dipped into the coating solution during coating on the mass of material coated on floss. (FIG. 12A.1) Effect of number of times the floss is dipped into the coating solution during coating on the mass of free sulforhodamine coated on floss. (FIG. 12A.2) Effect of number of times the floss is dipped into the coating solution during coating on the mass of sulforhodamine encapsulated in poly(lactic-co-glycolic) acid nanoparticles coated on floss. (FIG. 12A.3) Effect of number of times the floss is dipped into the coating solution during coating on the mass of coumarin six encapsulated in poly(lactic-co-glycolic) acid nanoparticles coated on floss.

FIG. 13A.1 to 13A.3 show effect of concentration of drug in the coating solution on the mass of material coated on floss. (FIG. 12A.1) Effect of concentration of free sulforhodamine in the coating solution on its mass coated on floss. (FIG. 12A.2) Effect of concentration of sulforhodamine encapsulated in poly(lactic-co-glycolic) acid nanoparticles in the coating solution on its mass coated on floss. (FIG. 12A.3) Effect of concentration of coumarin 6 encapsulated in poly(lactic-co-glycolic) acid nanoparticles in the coating solution on its mass coated on floss.

FIG. 14A to 14H show coating of the floss with two different layers each containing a separate drug. (FIG. 14A) Scanning electron micrograph of the surface of floss first coated with poly(lactic-co-glycolic) acid polymer layer containing coumarin 6 on top of which sulforhodamine encapsulated in poly(lactic-co-glycolic) acid nanoparticles were coated. This image is before flossing porcine teeth. (FIG. 14B) Scanning electron micrograph of the cross-section of floss first coated with poly(lactic-co-glycolic) acid polymer layer containing coumarin 6 on top of which sulforhodamine encapsulated in poly(lactic-co-glycolic) acid nanoparticles were coated. This image is before flossing porcine teeth. (FIG. 14C) Fluorescent micrograph of the surface of floss first coated with poly(lactic-co-glycolic) acid polymer layer containing coumarin 6 on top of which sulforhodamine encapsulated in poly(lactic-co-glycolic) acid nanoparticles were coated. This image is before flossing porcine teeth. (FIG. 14D) Fluorescent micrograph of the cross-section of floss first coated with poly(lactic-co-glycolic) acid polymer layer containing coumarin 6 on top of which sulforhodamine encapsulated in poly(lactic-co-glycolic) acid nanoparticles were coated. This image is before flossing porcine teeth. (FIG. 14E) Scanning electron micrograph of the surface of floss first coated with poly(lactic-co-glycolic) acid polymer layer containing coumarin 6 on top of which sulforhodamine encapsulated in poly(lactic-co-glycolic) acid nanoparticles were coated. This image is after flossing porcine teeth. (FIG. 14F) Scanning electron micrograph of the cross-section of floss first coated with poly(lactic-co-glycolic) acid polymer layer containing coumarin 6 on top of which sulforhodamine encapsulated in poly(lactic-co-glycolic) acid nanoparticles were coated. This image is after flossing porcine teeth. (FIG. 14G) Fluorescent micrograph of the surface of floss first coated with poly(lactic-co-glycolic) acid polymer layer containing coumarin 6 on top of which sulforhodamine encapsulated in poly(lactic-co-glycolic) acid nanoparticles were coated. This image is after flossing porcine teeth. (FIG. 14H) Fluorescent micrograph of the cross-section of floss first coated with poly(lactic-co-glycolic) acid polymer layer containing coumarin 6 on top of which sulforhodamine encapsulated in poly(lactic-co-glycolic) acid nanoparticles were coated. This image is after flossing porcine teeth.

FIG. 15A to 15H show visual proof of delivery from floss coated with two different layers each containing a separate drug. (FIG. 15A) Photograph of porcine teeth before flossing. (FIG. 15B) Fluorescent micrograph of porcine teeth before flossing as seen in the coumarin 6 optical filter. (FIG. 15C) Fluorescent micrograph of porcine teeth before flossing as seen in the sulforhodamine optical filter. (FIG. 15D) Fluorescent micrograph of porcine teeth before flossing as seen in the coumarin 6+sulforhodamine optical filter. (FIG. 15E) Photograph of porcine teeth 24 h after flossing. (FIG. 15F) Fluorescent micrograph of porcine teeth 24 h after flossing as seen in the coumarin 6 optical filter. (FIG. 15G) Fluorescent micrograph of porcine teeth 24 h after flossing as seen in the sulforhodamine optical filter. (FIG. 15H) Fluorescent micrograph of porcine teeth 24 h after flossing as seen in the coumarin 6+sulforhodamine optical filter.

FIG. 16A to 16E show visual proof of delivery from floss coated with two different layers each containing a separate drug. Visivalization was done by extracting the tooth and looking at gum pocket and tooth. (FIG. 16A) Scheme of cutting gum to extract the tooth and gum tissue. (FIG. 16B) Bright field photograph of the extracted gum and the tooth. (FIG. 16C) Fluorescent micrograph of extracted gum and the tooth as seen in the coumarin 6 optical filter. (FIG. 16D) Fluorescent micrograph of extracted gum and the tooth as seen in the sulforhodamine optical filter. (FIG. 16E) Fluorescent micrograph of extracted gum and the tooth as seen in the coumarin 6+sulforhodamine optical filter.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Periodontal, or gum disease, is a deleterious process caused by polymicrobial infection coupled with an overactive and destructive inflammatory immune response. The disease process affects 47.2% of adults over 30 years of age and 70% of people 65+years old[1]. Periodontal disease, as an inflammatory condition is a continuum of gingivitis and periodontitis disease and is a major cause of tooth loss and to some extent facial disfiguration[2]. The disease process negatively effects nutrition, self-esteem, and quality of life. Moreover, it is known to lead to heart disease, diabetes, and even death.[3] Microbes penetrate the gingival margin and through fermentation generate a plaque biofilm thus initiating an immune response. The inflammatory response becomes overactive resulting in destruction of tooth, gum tissue, and alveolar bone. Treatment of periodontitis consists of a variety of techniques such as: (1) professional cleaning and removal of plaque, (2) Scaling/Root Planning (SRP), (3) medication coupled with SRP (4), light therapy (laser), or (5) surgical removal and tissue grafting. However, due to bacterial persistence and reintroduction, management of the disease process best characterizes treatment. Data shows floss is recommended where gingival health treatment is required and the use of local or systemic anti-inflammatory agents has no robust data[4]. Moreover, there exists no data for the direct comparison of medicinal delivery formats. Selection of delivery format is currently dependent upon the agent to be delivered and relevant factors such as cost, ease of access and patient compliance must also be considered. Therefore, to address ease of treatment and accessibility, patient compliance, and create a ubiquitous format of delivery, the present inventors developed an engineered, tailorable medically-coated floss. Floss coated with a specific medication is expected to be able address a microbe infection and inflammation process by releasing the medical coating to the local area as well as to mechanically remove and control plaque. This application will medically address the condition in addition to removing the irritant.

The present invention provides a ubiquitous treatment for gum disease. Gum disease is a deleterious process caused by a polymicrobial infection coupled with a destructive immune response. This causes loss of teeth, jaw bone, self esteem and malnourishment. Gum disease is also known the lead to diabetes, heart disease and even death. Gum disease is a continuum of gingivitis and periodontitis. Microbes process sugars in the mouth, take up residence upon the teeth and within the gum line, and initiate an exaggerated immune response. These microbes are persistent and resistant to drugs. A patient has to repeatedly go to the dentist for treatment. Through use of this floss patients can receive treatment at home at their convenience.

Treatment of the disease is best addressed as a management issue. The specifically tailorable medicated floss of the present invention provides a painless localized delivery of medicine to treat the infected area as well as slow the inflammation. Moreover, it is also able to mechanically remove the biofilm (plaque) that is generated by the disease process and thus cleans the infected area and removes the continuous irritant. Perhaps most ideal about the present invention is the convenience it offers the patient. The medicated floss can be taken home and utilized as a home treatment and not require a visit to the dentist for a daily/weekly treatment.

The present invention overcomes the following problems with the prior art: (1) eliminates the need for professional cleaning and scaling/root planing because this requires a visit to a professional and is therefore inconvenient and often avoided by patients. (2) Eliminates the need for systemic medication, which due to the lack of vascularization and obstructive nature of the microbial biofilm, often cannot reach the microbe, thus local delivery is better as the inventors are proposing with the floss. (3) Medicated gel is not efficient for local delivery because: (a) it is easily lost from the gum line due to its amorphous nature; (b) does not readily disrupt the bacterial biofilm which is required for disease eradication; (c) requires professional assistance for application/re-application. (4) Blue light therapy (otherwise known as laser light or Er:YAG light therapy) is not effective on all microbes but rather only the ones that contain pigment molecules. (5) surgical removal of necrotic tissue, tooth, and jaw leaves the individual physical disfigured.

As used herein, the term "biodegradable" refers to materials that, when introduced into cells, are broken down into components that cells can either reuse or dispose of without significant toxic effects on the cells. A material may be biodegradable by any mechanism, e.g., dissolution in an aqueous environment, enzymatic degradation, hydrolysis, and/or combinations thereof. The biodegradable components generated by breakdown of a biodegradable material are biocompatible and therefore do not induce significant inflammation and/or other adverse effects in vivo. Biodegradable polymer materials break down into their component monomers. In some embodiments, breakdown of biodegradable materials (including, for example, biodegradable polymer materials) involves hydrolysis of ester bonds. Biodegradable polymers include, for example, polymers of hydroxy acids such as lactic acid and glycolic acid, including but not limited to poly(hydroxyl acids), poly(lactic acid)_(PLA), poly(glycolic acid)_(PGA), poly(lactic-co-glycolic acid)(PLGA), and copolymers with polyethyleneglycol (PEG), polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof.

In some embodiments, the coating and/or the encapsulant can include one or more polymers selected from the group consisting of poly(hydroxy acids) such as poly(lactic acid), poly(glycolic acid), poly(lactic acid-co-glycolic acid), poly (lactic-co-glycolic acid), and derivatives of poly(lactic-co-glycolic acid), PEGylated poly(lactic-co-glycolic acid), poly (lactide), poly(glycolide), poly(lactide-co-glycolide), poly (anhydrides), PEGylated poly(anhydrides), poly (ortho esters), derivatives of poly(ortho esters), PEGylated poly (ortho esters), poly(caprolactones), derivatives of poly (caprolactone), PEGylated poly(caprolactones), polyamines (e.g. spermine, spermidine, polylysine, and derivatives thereof), PEGylated polylysine, polyamides, polycarbonates, poly(propylene fumarates), polyamides, polyphosphazenes, polyamino acids, polyethers, polyacetals, polylactides, polyhydroxyalkanoates, polyglycolides, polyketals, polyesteramides, poly(dioxanones), polyhydroxybutyrates, polyhydroxyvalyrates, polycarbonates, polyorthocarbonates, poly(vinyl pyrrolidone), polycyanoacrylates, polyalkylene oxalates, polyalkylene succinates, poly(malic acid), poly(methyl vinyl ether), poly(ethylene imine), poly(acrylic acid), poly(maleic anhydride), poly(ethylene imine), derivatives of poly(ethylene imine), PEGylated poly(ethylene imine), poly(acrylic acid), derivatives of poly(acrylic acid), PEGylated poly(acrylic acid), poly(urethane), PEGylated poly(urethane), derivatives of poly(urethane), poly(lactide), poly(glycolide), poly(hydroxy acids), polyesters, poly(arylates), polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxy-propyl cellulose, hydroxy-propyl methyl cellulose, hydroxy-butyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone) and/or derivatives thereof.

In some embodiments, the coating and/or the encapsulant can include of one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and/or combinations thereof.

In some embodiments, the coating and/or the encapsulant can include one or more natural polymers. Exemplary natural polymers include, but are not limited to, proteins (such as albumin, collagen, gelatin), prolamines (for example, zein), polysaccharides (such as alginate), cellulose derivatives (such as hydroxypropyl cellulose, sodium carboxymethyl cellulose, ethyl cellulose and cellulose acetate), polyhydroxyalkanoates (for example, polyhydroxybutyrate), and/or combinations thereof. In some embodiments, a natural polymer may comprise or consist of chitosan.

In some embodiments, the coating and/or the encapsulant can include one or more polymers such as PLGA copolymerized with polyethylene glycol (PEG). Without wishing to be bound by any particular theory, it is proposed that arrangement of a nanoparticle so that PEG is exposed on the external surface, may increase stability of the nanoparticle in blood, perhaps at least in part due to the hydrophilicity of PEG.

As used herein, the term "medicament" or "biologically active agent" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

As used herein, the term "encapsulated" refers to substances that are completely surrounded by another material, such as a biodegradable coating, material, or polymer.

As used herein, the terms "treatment", "treat", or "treating" refers to any administration of a substance that partially or completely alleviates, ameliorates, relives, inhibits, delays onset of, reduces severity of, and/or reduces frequency, incidence or severity of one or more symptoms, features, and/or causes of gum disease, disorders, and/or conditions. Such treatment may be of a subject who does not exhibit signs of the relevant disease, disorder and/or condition and/or of a subject who exhibits only early signs of gum disease. Alternatively or additionally, such treatment may be of a subject who exhibits one or more established signs of the relevant disease, disorder and/or condition. In some embodiments, treatment may be of a subject who has been diagnosed as suffering from the gum disease. In some embodiments, treatment may be of a subject known to have one or more susceptibility factors that are statistically correlated with increased risk of development of gum disease.

Three-inch lengths of unwaxed nylon braided floss were stretched and precoated with a substrate base layer of poly lactic-co-glycolic acid (PLGA) (MW 44,000 kDa) dissolved in dichloromethane (175 mg/ml) by dipping the stretched layer into the PLGA solution. Upon drying the precoated lengths were dip-coated three times with sulforhodamine-B entrapped nanoparticles (NP) (7.25 mg/ml) and allowed 15 min to dry between coating steps. Sulforhodamine-B was encapsulated in PLGA using a double emulsion technique. Particle size was determined using dynamic light scattering. Similarly, free sulforhodamine (480 μg/ml) in coating solution was also coated upon pretreated floss. Using a freshly excised porcine lower jaw (immediately after euthanasia so as to best replicate natural in vivo conditions), the entire 3-inch length of coated floss was passed within the gum line and tooth three times in order to best replicate the natural flossing method and relieve the nanoparticle payload from the floss. The porcine jaw was then placed on a raised platform in a pan filled with deionized (DI) water and allowed to incubate at 37° C. for 24 hours. Using a camera, images were taken during the coating procedure as well as during the flossing process. Images were captured of the lower jaw immediately after flossing as well as after the 24 hr incubation period using a stereomicroscope. Loading efficiency of sulforhodamine-B in PLGA particles, amount coated on floss and delivery efficiency of floss payload to the gum line was calculated using a spectrophotometer (565 ex/586 em) and a previously established standard curve. Specifically, during delivery efficiency analysis, a mass balance was conducted. Samples of sulforhodamine-B particles after delivery were collected from the tooth and gum surface using premoistened cotton tip and homogenized in 70 μl dimethylsufoxide sample concentration measurements were taken. The mass of sulforhodamine-B remaining on the floss was calculated and the remaining amount was assumed trapped in the target area and inaccessible within the gum line. Similarly coumarin 6 (490ex/518em) was quantified.

Figure 1B:
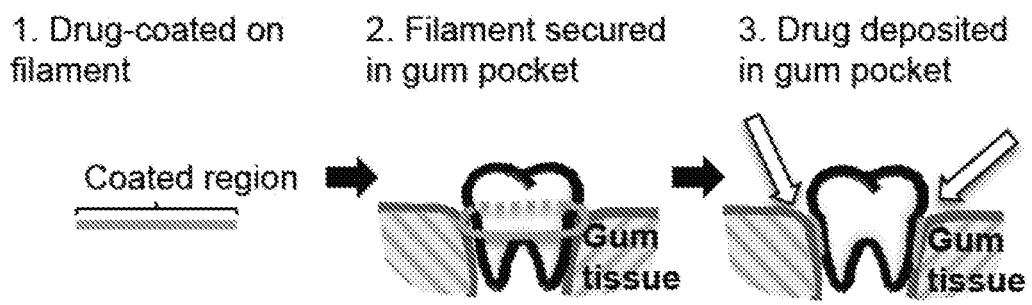

Sulforhodamine-B and coumarin 6 entrapped nanoparticles possessed a diameter of about 140-200 nm and a loading efficiency of 6.67%. The concept of using floss for delivery into the gums is shown in FIGS. 1A and 1B. In addition to using the coated floss in the traditional manner in which a flossing motion is used (FIG. 1A), the coated floss can also be placed and situated in the gum space in a stationary manner for a prolonged duration of time (FIG. 1B). Examples of different filaments that can be used in this delivery approach are shown in FIG. 2: floss in the form of a tape (FIG. 2A), braided floss (FIG. 2B), and a suture (FIG. 2C). A braided floss was coated with pure sulforhodamine (FIG. 3A) or sulforhodamine encapsulated in PLGA (FIG. 3B). The delivery efficiency from free sulforhodamine braided floss was about 22% in the gum (FIG. 4A). About 65% still remained on the floss (FIG. 4A). Similarly the delivery efficiency from nanoparticles encapsulating sulforhodamine was also around 25% (FIG. 4B) and about 44% nanoparticles were still on the floss (FIG. 4B). Examination of the floss after performing flossing showed that nanoparticles were stuck in the spaces between individual filaments of the braided floss (FIG. 3B.3). To improve the delivery efficiency we coated the floss with PLGA to fill the void spaces between the individual filaments of the braided floss. Before coating the PLGA layer microscopic voids were visible between the individual filaments (FIG. 5A.1, 5A.2). After the PLGA precoat, these void spaces were filled (FIG. 5A.3, 5A.4, 5A.5, 5A.6). When we coated free sulforhodamine (FIG. 6A.1, 6A.2, 6A.3) and flossed porcine teeth (FIG. 6A.4, 6A.5, 6A.6) the delivery efficiency was about 19% and not significantly different as compared to the delivery efficiency when free sulforhodamine was coated on the braided floss that did not contain a PLGA precoat (FIG. 4A). When we coated nanoparticles encapsulating sulforhodamine (FIG. 7A.1, 7A.2, 7A.3) and flossed porcine teeth (FIG. 7A.4, 7A.5, 7A.6) the delivery efficiency was about 91% and significantly higher as compared to the delivery efficiency when nanoparticles encapsulating sulforhodamine were coated on the braided floss that did not contain a PLGA precoat (FIG. 4B). To determine whether free sulforhodamine can be delivered into porcine gum pocket and can then diffuse into the gum tissue we visually examined porcine teeth before (FIGS. 8A.1 and 8A.2) and 24 h after flossing (FIGS. 8A.3 and 8A.4). Sulforhodamine was seen to diffuse into the gum tissue (FIGS. 8A.3 and 8A.4). Similarly, to determine whether nanoparticles encapsulating sulforhodamine can be delivered into porcine gum pocket and sulforhodamine can then diffuse into the gum tissue we visually examined porcine teeth before (FIGS. 9A.1 and 9A.2) and 24 h after flossing (FIGS. 9A.3 and 9A.4). To further confirm delivery of nanoparticles we made a precision cut between the flossed and the adjacent non-flossed tooth to bisect the gum tissue. Sulforhodamine was seen to diffuse deep into the gum tissue (FIGS. 9A.5 and 9A.6). Sulforhodamine is a water-soluble molecule. To assess delivery of a water insoluble molecule we used coumarin 6. We coated nanoparticles encapsulating coumarin 6 on floss precoated with PLGA (FIG. 10A.1, 10A.2, 10A.3) and flossed porcine teeth (FIG. 10A.4, 10A.5, 10A.6) and the delivery efficiency was about 82%. (FIG. 10A.7). To confirm delivery of nanoparticles we made a precision cut between the flossed and the adjacent non-flossed tooth to remove the tooth from the gum space (FIG. 11A). Nanoparticles containing coumarin 6 were seen deposited in the gum pocket space and tooth surface (FIGS. 11B.1 and 11B.2). To perform clinically relevant dosage the amount to be delivered will need to be tuned in varying amounts depending upon the active drug or material that will need to be delivered. First the number of times the floss was dipped in the coating solution was increased from 5 to 10 to 20. As the number of dips increased the mass of free sulforhodamine (FIG. 12A), sulforhodamine encapsulated in PLGA nanoparticles (FIG. 12B), and coumarin 6 encapsulated in PLGA nanoparticles (FIG. 12C) increased. Next the mass of free sulforhodamine (FIG. 13A), sulforhodamine encapsulated in PLGA nanoparticles (FIG. 13B), or coumarin 6 encapsulated in PLGA nanoparticles (FIG. 13C) in the coating solution was increased. The amount of free sulforhodamine (FIG. 13A), sulforhodamine encapsulated in PLGA nanoparticles (FIG. 13B), or coumarin 6 encapsulated in PLGA nanoparticles (FIG. 13C) coated on the floss increased with an increase in their respective amounts in the coating solution. For various reasons there may be a need to add drug or other active ingredient into the precoat layer. For example, to fight bacterial infection in the gum from different bacterial strains different antibacterial agents might be required. In another example mixing of two antibacterial agents might be incompatible. For such instances it may be an option to include drug in the precoat layer formed over the floss. Coumarin six in its free-form was mixed into the PLGA coating solution and the floss was precoated. On top of this precoat containing coumarin 6, nanoparticles encapsulating sulforhodamine were coated. This dual drug coated floss was examined before and after flossing. Before flossing a uniform coating was seen through scanning electron imaging (FIG. 14A, 14B). Individual coatings for each drug could be seen in the appropriate optical filters using fluorescent imaging (FIG. 14C, 14D). After flossing removal of both the top and the precoat layer were seen (FIG. 14E, 14F, 14G, 14H). To determine whether coumarin 6 in the PLGA precoat layer and sulforhodamine from the nanoparticles in the top layer can be diffuse into the gum tissue we imaged porcine teeth before (FIGS. 15A, 15B, 15C, 15D) and 24 h after flossing (FIG. 15E, 15F, 15G, 15H). Sulforhodamine and coumarin were both seen to diffuse into the gum tissue (FIG. 15E, 15F, 15G, 15H). To confirm delivery of both the drugs, i.e., sulforhodamine and coumarin 6, we made a precision cut between the flossed and the adjacent non-flossed tooth to remove the tooth from the gum space (FIG. 16A). PLGA layer containing free coumarin 6 and nanoparticles containing sulforhodamine were seen deposited in the gum pocket space and tooth surface (FIG. 16B, 16C, 16D, 16E).

These data demonstrate that the floss can be coated with free drug, drug encapsulated in nanoparticles, or drug encapsulated in the precoat layer or a combination thereof. It was found that nanoparticles were getting stuck in the space between individual filaments comprising the braided floss. The precoat layer, in this example case being made of PLGA was able to fill the white spaces and prevented the nanoparticles from getting trapped in these white spaces. The precoat layer increase the delivery efficiency to greater than 90%. Different imaging and visualization techniques confirmed that the material coated on the floss can indeed be delivered into the common space and this material can subsequently diffuse into the gum tissue. The mass of material coated on the floss can be tuned by controlling the coating process such as by increasing the mass of the active material in the coating solution or by increasing the number of times the floss is dipped into the coating solution. The preparation and coating techniques provided an innovative modality for gum disease management.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method of treating a gum disease, the method comprising:
    (i) providing a flexible filament coated with a precoat layer comprising a first drug, and wherein at least part of said precoated filament is subsequently uniformly coated with polymer nanoparticles comprising a second drug, and wherein the precoated filament is coated with said polymer nanoparticles at least 5 times if the second drug is water-soluble, and at least 20 times if the second drug is not water-soluble; and wherein the first drug and the second drug can be the same or different;
    (ii) inserting said flexible filament into a gum pocket; and
    (iii) moving said flexible filament in the gum pocket at least once to deposit at least part of the drugs from the flexible filament into the gum pocket.

2. The method of claim 1, wherein the filament is selected from a thread, a floss, or a suture.

3. The method of claim 1, wherein the filament is a floss selected from unwaxed, waxed, braided, non-braided, monolithic, tape, or a combination thereof.

4. The method of claim 1, wherein the coated portion of the filament is moved more than once in and out of the gum pocket.

5. The method of claim 1, wherein the filament is of monolithic construction or comprises two or more filaments braided together.

6. The method of claim 1, wherein the drug is selected from an antibiotic, an antiinflammatory, an antimicrobial, an antifungal, an antibody, a steroid, an antiparasitic, an antiamoebic, an antihelminthic, an antiprotozoal, an antinematode, an anticestode, an antitrematode, or mixtures thereof.

7. The method of claim 6, wherein the antibiotic is selected from the group consisting of amikacin, betamethasone, clindamycin, clotrimazole, gentamicin, kanamycin, minocycline, oxytetracycline, penicillin, tetracycline and mixtures thereof.

8. The method of claim 1, wherein the second drug is encapsulated in the polymer nanoparticles.

9. The method of claim 1, wherein the precoat layer contains the first drug either in free form, after entrapment in particles, encapsulated, or a combination thereof.

10. The method of claim 1, further comprising securing the filament in the gum pocket for a pre-determined duration of time.

\* \* \* \* \*